United States Patent
Dabrowiak (10) Patent No.: US 10,828,189 B2
(45) Date of Patent: *Nov. 10, 2020

(54) HEAT EXCHANGE SYSTEM FOR PATIENT TEMPERATURE CONTROL WITH MULTIPLE COOLANT CHAMBERS FOR MULTIPLE HEAT EXCHANGE MODALITIES

(71) Applicant: ZOLL CIRCULATION, INC., San Jose, CA (US)

(72) Inventor: Jeremy Thomas Dabrowiak, Santa Clara, CA (US)

(73) Assignee: Zoll Circulation Inc., San Jose, CA (US)

( * ) Notice: Subject to any disclaimer, the term of this patent is extended or adjusted under 35 U.S.C. 154(b) by 768 days.

This patent is subject to a terminal disclaimer.

(21) Appl. No.: 15/332,519

(22) Filed: Oct. 24, 2016

(65) Prior Publication Data

US 2017/0035604 A1 Feb. 9, 2017

Related U.S. Application Data

(63) Continuation of application No. 14/175,545, filed on Feb. 7, 2014, now Pat. No. 9,474,644.

(51) Int. Cl.
*A61F 7/00* (2006.01)
*A61F 7/12* (2006.01)
(Continued)

(52) U.S. Cl.
CPC .............. *A61F 7/0085* (2013.01); *A61F 7/02* (2013.01); *A61F 7/12* (2013.01); *F28D 9/0068* (2013.01);
(Continued)

(58) Field of Classification Search
CPC .. A61F 7/0085; A61F 7/02; A61F 7/12; A61F 2007/126; A61F 2007/0054; F28D 9/0081; F28D 9/0075; F28D 9/0068
See application file for complete search history.

(56) References Cited

U.S. PATENT DOCUMENTS 1,459,112 A    6/1923  Mehl
1,726,761 A    9/1929  Palmer
(Continued)

FOREIGN PATENT DOCUMENTS

CN    101090685 A    12/2007
DE    19531935 A1    2/1997
(Continued)

OTHER PUBLICATIONS

Jeremy Thomas Dabrowiak, Craig Wendell Pendry, Christoph Matthias Pistor, "Patient Heat Exchange System With Two and Only Two Fluid Loops", File History of related pending U.S. Appl. No. 14/180,719, filed Feb. 14, 2014.
(Continued)

*Primary Examiner* — Kaitlyn E Smith
*Assistant Examiner* — Yasamin Ekrami
(74) *Attorney, Agent, or Firm* — Fish & Richardson P.C.

(57) ABSTRACT

Cold plates through which refrigerant flows define a slot between them that can receive a cassette through which sterile working fluid with a relatively low flow rate flows from an intravascular heat exchange catheter. The working fluid from the catheter is heated or cooled by heat exchange with the cold plates through the walls of the cassette to maintain the sterility of the working fluid. On the other hand, high flow rate working fluid chambers surround the cold plates and non-sterile working fluid from an external heat exchange pad flows through the high flow rate working fluid chambers to exchange heat through direct contact with the cold plates.

19 Claims, 5 Drawing Sheets

(51) Int. Cl.
   *A61F 7/02* (2006.01)
   *F28D 9/00* (2006.01)
(52) U.S. Cl.
   CPC ......... *F28D 9/0075* (2013.01); *F28D 9/0081* (2013.01); *A61F 2007/0054* (2013.01); *A61F 2007/126* (2013.01)

(56) References Cited

U.S. PATENT DOCUMENTS

| | | |
|---|---|---|
| 1,857,031 A | 5/1932 | Schaffer |
| 2,223,688 A | 12/1940 | Otto |
| 2,663,030 A | 12/1953 | Dahlberg |
| 2,673,987 A | 4/1954 | Upshaw et al. |
| 2,987,004 A | 6/1961 | Murray |
| 3,140,716 A | 7/1964 | Harrison et al. |
| 3,225,191 A | 12/1965 | Calhoun |
| 3,228,465 A | 1/1966 | Louis |
| 3,369,549 A | 2/1968 | Armao |
| 3,425,419 A | 2/1969 | Dato |
| 3,504,674 A | 4/1970 | Swenson et al. |
| 3,726,269 A | 4/1973 | Webster |
| 3,744,555 A | 7/1973 | Fletcher et al. |
| 3,751,077 A | 8/1973 | Hiszpanski |
| 3,834,396 A | 9/1974 | Foster |
| 3,937,224 A | 2/1976 | Uecker |
| 3,945,063 A | 3/1976 | Matsuura |
| 4,038,519 A | 7/1977 | Foucras |
| 4,065,264 A | 12/1977 | Lewin |
| 4,103,511 A | 8/1978 | Kress et al. |
| 4,126,132 A | 11/1978 | Portner et al. |
| 4,153,048 A | 5/1979 | Magrini |
| 4,173,228 A | 11/1979 | Van Steenwyk et al. |
| 4,181,132 A | 1/1980 | Parks |
| 4,181,245 A | 1/1980 | Garrett et al. |
| 4,259,961 A | 4/1981 | Hood |
| 4,298,006 A | 11/1981 | Parks |
| 4,459,468 A | 7/1984 | Bailey |
| 4,532,414 A | 7/1985 | Shah et al. |
| 4,552,516 A | 11/1985 | Stanley |
| 4,554,793 A | 11/1985 | Harding, Jr. |
| 4,558,996 A | 12/1985 | Becker |
| 4,581,017 A | 4/1986 | Sahota |
| 4,638,436 A | 1/1987 | Badger et al. |
| 4,653,987 A | 3/1987 | Tsuji et al. |
| 4,661,094 A | 4/1987 | Simpson |
| 4,665,391 A | 5/1987 | Spani |
| 4,672,962 A | 6/1987 | Hershenson |
| 4,754,752 A | 7/1988 | Ginsburg et al. |
| 4,787,388 A | 11/1988 | Hofmann |
| 4,813,855 A | 3/1989 | Leveen et al. |
| 4,849,196 A | 7/1989 | Yamada et al. |
| 4,852,567 A | 8/1989 | Sinofsky |
| 4,860,744 A | 8/1989 | Johnson et al. |
| 4,869,250 A | 9/1989 | Bitterly |
| 4,906,237 A | 3/1990 | Johansson et al. |
| 4,925,376 A | 5/1990 | Kahler |
| 4,941,475 A | 7/1990 | Williams et al. |
| 5,080,089 A | 1/1992 | Mason et al. |
| 5,092,841 A | 3/1992 | Spears |
| 5,103,360 A | 4/1992 | Maeda |
| 5,106,360 A | 4/1992 | Ishiwara et al. |
| 5,174,285 A | 12/1992 | Fontenot |
| 5,192,274 A | 3/1993 | Bierman |
| 5,195,965 A | 3/1993 | Shantha |
| 5,211,631 A | 5/1993 | Sheaff |
| 5,263,925 A | 11/1993 | Gilmore et al. |
| 5,269,758 A | 12/1993 | Taheri |
| 5,281,215 A | 1/1994 | Milder |
| 5,304,214 A | 4/1994 | DeFord et al. |
| 5,342,301 A | 8/1994 | Saab |
| 5,344,436 A | 9/1994 | Fontenot et al. |
| 5,370,675 A | 12/1994 | Edwards et al. |
| 5,383,856 A | 1/1995 | Bersin |
| 5,391,030 A | 2/1995 | Lee |
| 5,403,281 A | 4/1995 | O'Neill et al. |
| 5,433,588 A | 7/1995 | Monk |
| 5,433,740 A | 7/1995 | Yamaguchi |
| 5,437,673 A | 8/1995 | Baust et al. |
| 5,458,639 A | 10/1995 | Tsukashima et al. |
| 5,476,368 A | 12/1995 | Rabenau |
| 5,486,207 A | 1/1996 | Mahawili |
| 5,486,208 A | 1/1996 | Ginsburg |
| 5,507,792 A | 4/1996 | Mason et al. |
| 5,531,714 A | 7/1996 | Dahn et al. |
| 5,531,776 A | 7/1996 | Ward et al. |
| 5,624,392 A | 4/1997 | Saab |
| 5,634,907 A | 6/1997 | Rani et al. |
| 5,676,670 A | 10/1997 | Kim |
| 5,693,344 A | 12/1997 | Knight et al. |
| 5,701,905 A | 12/1997 | Esch |
| 5,706,889 A | 1/1998 | Bach et al. |
| 5,709,564 A | 1/1998 | Yamada et al. |
| 5,709,654 A | 1/1998 | Klatz et al. |
| 5,716,386 A | 2/1998 | Ward et al. |
| 5,730,720 A | 3/1998 | Sites et al. |
| 5,733,319 A | 3/1998 | Neilson et al. |
| 5,737,782 A | 4/1998 | Matsuura et al. |
| 5,746,585 A | 5/1998 | McDunn et al. |
| 5,759,017 A | 6/1998 | Patton et al. |
| 5,776,079 A | 7/1998 | Cope et al. |
| 5,788,647 A | 8/1998 | Eggers |
| 5,803,324 A | 9/1998 | Silberman |
| 5,837,003 A | 11/1998 | Ginsburg |
| 5,857,843 A | 1/1999 | Leason et al. |
| 5,862,675 A | 1/1999 | Scaringe et al. |
| 5,875,282 A | 2/1999 | Jordan et al. |
| 5,879,329 A | 3/1999 | Ginsburg |
| 5,895,418 A | 4/1999 | Saringer |
| 5,908,407 A | 6/1999 | Frazee et al. |
| 5,957,963 A | 9/1999 | Dobak |
| 5,980,561 A | 11/1999 | Kolen et al. |
| 5,989,238 A | 11/1999 | Ginsburg |
| 6,019,783 A | 2/2000 | Philips et al. |
| 6,042,559 A | 3/2000 | Dobak |
| 6,051,019 A | 4/2000 | Dobak |
| 6,059,825 A | 5/2000 | Hobbs et al. |
| 6,096,068 A | 8/2000 | Dobak et al. |
| 6,110,139 A | 8/2000 | Loubser |
| 6,110,168 A | 8/2000 | Ginsburg |
| 6,117,065 A | 9/2000 | Hastings et al. |
| 6,117,105 A | 9/2000 | Bresnaham et al. |
| 6,124,452 A | 9/2000 | DiMagno |
| 6,126,684 A | 10/2000 | Gobin et al. |
| 6,146,141 A | 11/2000 | Schumann |
| 6,146,411 A | 11/2000 | Noda et al. |
| 6,148,634 A | 11/2000 | Sherwood |
| 6,149,670 A | 11/2000 | Worthen et al. |
| 6,149,673 A | 11/2000 | Ginsburg |
| 6,149,676 A | 11/2000 | Ginsburg |
| 6,149,677 A | 11/2000 | Dobak |
| 6,149,806 A | 11/2000 | Baer |
| 6,165,207 A | 12/2000 | Balding |
| 6,188,930 B1 | 2/2001 | Carson et al. |
| 6,197,045 B1 | 3/2001 | Carson et al. |
| 6,224,624 B1 | 5/2001 | Lasheras |
| 6,231,594 B1 | 5/2001 | Dae |
| 6,231,595 B1 | 5/2001 | Dobak |
| 6,235,048 B1 | 5/2001 | Dobak |
| 6,238,428 B1 | 5/2001 | Werneth |
| 6,245,095 B1 | 6/2001 | Dobak |
| 6,251,129 B1 | 6/2001 | Dobak |
| 6,251,130 B1 | 6/2001 | Dobak |
| 6,254,626 B1 | 7/2001 | Dobak |
| 6,261,312 B1 | 7/2001 | Dobak |
| 6,264,679 B1 | 7/2001 | Keller |
| 6,283,940 B1 | 9/2001 | Mulholland |
| 6,287,326 B1 | 9/2001 | Pecor |
| 6,290,717 B1 | 9/2001 | Philips et al. |
| 6,299,599 B1 | 10/2001 | Pham et al. |
| 6,306,161 B1 | 10/2001 | Ginsburg |
| 6,312,452 B1 | 11/2001 | Dobak |
| 6,325,818 B1 | 12/2001 | Werneth |
| 6,338,727 B1 | 1/2002 | Noda et al. |
| 6,364,899 B1 | 4/2002 | Dobak |

(56) References Cited

U.S. PATENT DOCUMENTS

| | | | |
|---|---|---|---|
| 6,368,304 B1 | 4/2002 | Aliberto |
| 6,375,674 B1 | 4/2002 | Carson et al. |
| 6,379,378 B1 | 4/2002 | Werneth |
| 6,383,144 B1 | 5/2002 | Mooney et al. |
| 6,383,210 B1 | 5/2002 | Magers |
| 6,393,320 B2 | 5/2002 | Lasersohn |
| 6,405,080 B1 | 6/2002 | Lasersohn |
| 6,409,747 B1 | 6/2002 | Gobin et al. |
| 6,416,533 B1 | 7/2002 | Gobin et al. |
| 6,419,643 B1 | 7/2002 | Shimada et al. |
| 6,428,563 B1 | 8/2002 | Keller |
| 6,450,990 B1 | 9/2002 | Walker et al. |
| 6,461,379 B1 | 10/2002 | Carson et al. |
| 6,464,666 B1 | 10/2002 | Augustine et al. |
| 6,464,716 B1 | 10/2002 | Dobak et al. |
| 6,527,798 B2 | 3/2003 | Ginsburg et al. |
| 6,530,946 B1 | 3/2003 | Noda et al. |
| 6,544,282 B1 | 4/2003 | Dae et al. |
| 6,551,309 B1 | 4/2003 | LePivert |
| 6,554,791 B1 | 4/2003 | Cartledge et al. |
| 6,582,387 B2 | 6/2003 | Derek |
| 6,605,106 B2 | 8/2003 | Schwartz |
| 6,610,083 B2 | 8/2003 | Keller et al. |
| 6,613,280 B2 | 9/2003 | Myrick |
| 6,620,187 B2 | 9/2003 | Carson et al. |
| 6,620,188 B1 | 9/2003 | Ginsburg et al. |
| 6,620,189 B1 | 9/2003 | Machold |
| 6,622,542 B2 | 9/2003 | Derek |
| 6,624,679 B2 | 9/2003 | Tomaiuolo et al. |
| 6,635,076 B1 | 10/2003 | Ginsburg |
| 6,635,079 B2 | 10/2003 | Ginsburg |
| 6,645,232 B2 | 11/2003 | Carson et al. |
| 6,648,905 B2 | 11/2003 | Hoglund |
| 6,660,027 B2 | 12/2003 | Gruszecki |
| 6,669,715 B2 | 12/2003 | Hoglund |
| 6,673,098 B1 | 1/2004 | Machold |
| 6,675,835 B2 | 1/2004 | Gerner |
| 6,679,906 B2 | 1/2004 | Hammack et al. |
| 6,685,731 B2 | 2/2004 | Kushnir et al. |
| 6,685,733 B1 | 2/2004 | Dae et al. |
| 6,692,518 B2 | 2/2004 | Carson et al. |
| 6,695,874 B2 | 2/2004 | Machold et al. |
| 6,706,060 B2 | 3/2004 | Tzeng et al. |
| 6,716,188 B2 | 4/2004 | Noda et al. |
| 6,719,723 B2 | 4/2004 | Werneth |
| 6,719,779 B2 | 4/2004 | Daoud |
| 6,726,653 B2 | 4/2004 | Noda et al. |
| 6,733,495 B1 | 5/2004 | Bek |
| 6,740,109 B2 | 5/2004 | Dobak |
| 6,743,201 B1 | 6/2004 | Dönig et al. |
| 6,764,391 B1 | 7/2004 | Grant |
| 6,799,063 B2 | 9/2004 | Carson et al. |
| 6,799,342 B1 | 10/2004 | Jarmon |
| 6,802,855 B2 | 10/2004 | Ellingboe |
| 6,818,012 B2 | 11/2004 | Ellingboe |
| 6,827,728 B2 | 12/2004 | Ellingboe |
| 6,843,099 B2 | 1/2005 | Derek |
| 6,843,800 B1 | 1/2005 | Dobak |
| 6,878,156 B1 * | 4/2005 | Noda ................. A61F 7/0085 |
| | | 607/104 |
| 6,887,263 B2 | 5/2005 | Bleam et al. |
| 6,890,347 B2 | 5/2005 | Machold |
| 6,893,419 B2 | 5/2005 | Noda et al. |
| 6,969,399 B2 | 11/2005 | Schock et al. |
| 6,974,435 B2 | 12/2005 | Derek |
| 6,997,942 B2 | 2/2006 | Machold |
| 7,070,612 B1 | 7/2006 | Collins et al. |
| 7,104,769 B2 | 9/2006 | Davis |
| 7,140,850 B2 | 11/2006 | Otis |
| 7,175,649 B2 | 2/2007 | Machold |
| 7,181,927 B2 | 2/2007 | Collins |
| 7,211,106 B2 | 5/2007 | Dobak |
| 7,247,165 B2 | 7/2007 | Machold |
| 7,258,662 B2 | 8/2007 | Machold |
| 7,357,786 B1 | 4/2008 | Bakke |
| 7,377,935 B2 | 5/2008 | Schock et al. |
| 7,510,569 B2 | 3/2009 | Dae et al. |
| 7,516,909 B2 | 4/2009 | Kaligain |
| 7,645,127 B2 | 1/2010 | Hagen |
| 7,658,755 B2 | 2/2010 | Machold |
| 7,666,215 B2 | 2/2010 | Callister et al. |
| 7,713,036 B2 | 5/2010 | Kojima et al. |
| 7,820,102 B2 | 10/2010 | Myrick |
| 7,822,485 B2 | 10/2010 | Collins |
| 7,846,193 B2 | 12/2010 | Dae et al. |
| 7,857,781 B2 | 12/2010 | Noda et al. |
| 7,879,077 B2 | 2/2011 | Machold |
| 7,892,269 B2 | 2/2011 | Collins et al. |
| 7,914,564 B2 | 3/2011 | Magers |
| 7,959,657 B1 * | 6/2011 | Harsy ................. A61F 7/007 |
| | | 607/104 |
| 7,963,986 B2 | 6/2011 | Machold |
| 8,105,262 B2 | 1/2012 | Noda et al. |
| 8,105,263 B2 | 1/2012 | Noda et al. |
| 8,105,264 B2 | 1/2012 | Noda et al. |
| 8,109,894 B2 | 2/2012 | Noda et al. |
| 8,128,384 B2 | 3/2012 | Mou |
| 8,177,824 B2 | 5/2012 | Machold |
| 8,226,605 B2 | 7/2012 | Faries et al. |
| 8,246,669 B2 | 8/2012 | Machold |
| 8,272,857 B2 | 9/2012 | Norman et al. |
| 8,366,667 B2 | 2/2013 | Chan |
| 8,551,151 B2 | 10/2013 | Machold |
| 8,740,959 B2 | 6/2014 | Machold |
| 8,784,464 B2 | 7/2014 | Machold |
| 8,888,729 B2 | 11/2014 | Noda |
| 9,345,614 B2 | 5/2016 | Schaefer |
| 9,474,644 B2 | 10/2016 | Dabrowiak |
| 9,492,633 B2 | 11/2016 | Dabrowiak |
| 9,675,756 B2 | 6/2017 | Kamen |
| 10,022,265 B2 | 7/2018 | Pamichev |
| 2001/0031946 A1 | 10/2001 | Walker et al. |
| 2001/0047196 A1 | 11/2001 | Ginsburg et al. |
| 2002/0004675 A1 | 1/2002 | Lasheras |
| 2002/0013569 A1 | 1/2002 | Sterman et al. |
| 2002/0022823 A1 | 2/2002 | Luo et al. |
| 2002/0096311 A1 | 7/2002 | Kushnir |
| 2002/0117559 A1 | 8/2002 | Kaligian |
| 2002/0134134 A1 | 9/2002 | Derek |
| 2002/0136662 A1 | 9/2002 | Myrick |
| 2002/0138034 A1 | 9/2002 | Derek |
| 2002/0145525 A1 | 10/2002 | Friedman et al. |
| 2002/0183692 A1 | 12/2002 | Callister |
| 2002/0198579 A1 | 12/2002 | Khanna |
| 2003/0036495 A1 | 2/2003 | Datta |
| 2003/0236496 A1 | 2/2003 | Elsner |
| 2003/0041911 A1 | 3/2003 | Gerner |
| 2003/0062090 A1 | 4/2003 | Secondo |
| 2003/0114795 A1 | 6/2003 | Durward |
| 2003/0135252 A1 * | 7/2003 | MacHold ............. A61M 25/10 |
| | | 607/106 |
| 2004/0013566 A1 | 1/2004 | Myrick |
| 2004/0019319 A1 | 1/2004 | Derek |
| 2004/0024437 A1 | 2/2004 | Machold |
| 2004/0026068 A1 | 2/2004 | Schmidt et al. |
| 2004/0244371 A1 | 2/2004 | Machold |
| 2004/0089050 A1 | 5/2004 | Derek |
| 2004/0089058 A1 | 5/2004 | Haan et al. |
| 2004/0102825 A1 | 5/2004 | Daoud |
| 2004/0104018 A1 | 6/2004 | Hughes et al. |
| 2004/0014331 A1 | 7/2004 | Machold |
| 2004/0143311 A1 | 7/2004 | Machold et al. |
| 2004/0154374 A1 | 8/2004 | Derek |
| 2004/0171935 A1 | 9/2004 | Van Creveld |
| 2004/0190255 A1 | 9/2004 | Cheon |
| 2004/0199230 A1 | 10/2004 | Yon |
| 2004/0210231 A1 | 10/2004 | Boucher et al. |
| 2004/0267340 A1 | 12/2004 | Cioanta |
| 2005/0065584 A1 | 3/2005 | Schiff |
| 2005/0137662 A1 | 6/2005 | Morris et al. |
| 2005/0156744 A1 | 7/2005 | Pires |
| 2005/0209658 A1 | 9/2005 | Machold |
| 2006/0030917 A1 | 2/2006 | Eccleston |
| 2006/0064146 A1 | 3/2006 | Collins |

(56) References Cited

U.S. PATENT DOCUMENTS

| | | | |
|---|---|---|---|
| 2006/0069418 A1* | 3/2006 | Schock | A61F 7/00 607/104 |
| 2006/0122673 A1 | 6/2006 | Callister et al. | |
| 2006/0210424 A1 | 9/2006 | Mallett et al. | |
| 2006/0241335 A1 | 10/2006 | Benkowski | |
| 2006/0253095 A1 | 11/2006 | Stull | |
| 2006/0293734 A1 | 12/2006 | Scott et al. | |
| 2007/0007640 A1 | 1/2007 | Harnden et al. | |
| 2007/0076401 A1 | 4/2007 | Carrez et al. | |
| 2007/0093710 A1 | 4/2007 | Maschke | |
| 2007/0156006 A1 | 7/2007 | Smith et al. | |
| 2007/0173759 A1* | 7/2007 | Augustine | A61F 7/0085 604/113 |
| 2007/0191918 A1 | 8/2007 | Machold | |
| 2007/0203552 A1 | 8/2007 | Machold | |
| 2007/0293919 A1 | 12/2007 | Machold | |
| 2008/0026068 A1 | 2/2008 | Schmidt | |
| 2008/0082051 A1 | 4/2008 | Miller et al. | |
| 2008/0114430 A1* | 5/2008 | Collins | A61F 7/12 607/106 |
| 2008/0119916 A1 | 5/2008 | Choucair et al. | |
| 2008/0230530 A1 | 9/2008 | Augustine et al. | |
| 2008/0262409 A1 | 10/2008 | Derrico et al. | |
| 2008/0267599 A1 | 10/2008 | Arnold et al. | |
| 2008/0269663 A1 | 10/2008 | Arnold | |
| 2009/0065565 A1 | 3/2009 | Cao | |
| 2009/0099518 A1 | 4/2009 | Magers | |
| 2009/0247963 A1 | 10/2009 | Bleam et al. | |
| 2009/0299287 A1 | 12/2009 | Carson et al. | |
| 2010/0036486 A1 | 2/2010 | Mazur | |
| 2010/0049119 A1 | 2/2010 | Norman et al. | |
| 2010/0082000 A1 | 4/2010 | Honeck et al. | |
| 2010/0129248 A1 | 5/2010 | Mou | |
| 2010/0204765 A1 | 8/2010 | Hall | |
| 2010/0256601 A1 | 10/2010 | Lippert et al. | |
| 2011/0022136 A1 | 1/2011 | Scott et al. | |
| 2011/0046551 A1 | 2/2011 | Augustine et al. | |
| 2011/0137249 A1 | 6/2011 | Collins et al. | |
| 2011/0184253 A1 | 7/2011 | Archer et al. | |
| 2011/0208276 A1 | 8/2011 | Machold | |
| 2011/0208277 A1 | 8/2011 | Machold | |
| 2011/0208278 A1 | 8/2011 | Machold | |
| 2011/0213305 A1* | 9/2011 | Jonsson | F28D 9/0087 604/113 |
| 2012/0095536 A1 | 4/2012 | Machold | |
| 2012/0100023 A1 | 4/2012 | Hanazuka et al. | |
| 2012/0158103 A1 | 6/2012 | Bledsoe | |
| 2012/0226338 A1 | 9/2012 | Machold | |
| 2013/0071270 A1 | 3/2013 | Zupp et al. | |
| 2013/0079855 A1 | 3/2013 | Helkowski | |
| 2013/0079856 A1 | 3/2013 | Dabrowiak | |
| 2013/0090708 A1 | 4/2013 | Dabrowiak | |
| 2013/0090709 A1 | 4/2013 | Machold | |
| 2013/0098880 A1 | 4/2013 | Korolev | |
| 2013/0150929 A1 | 6/2013 | Machold | |
| 2013/0150930 A1 | 6/2013 | Machold | |
| 2013/0172805 A1 | 7/2013 | Truckai | |
| 2013/0178923 A1 | 7/2013 | Dabrowiak | |
| 2013/0331774 A1 | 12/2013 | Farrell et al. | |
| 2013/0337732 A1 | 12/2013 | Williams et al. | |
| 2014/0081202 A1 | 3/2014 | Tsoukalis | |
| 2014/0094880 A1 | 4/2014 | Lim | |
| 2014/0094882 A1 | 4/2014 | Lim | |
| 2014/0094883 A1 | 4/2014 | Lim | |
| 2014/0276792 A1 | 9/2014 | Kaveckis | |
| 2014/0277302 A1 | 9/2014 | Weber | |
| 2014/0364928 A1 | 12/2014 | Machold | |
| 2015/0223974 A1 | 8/2015 | Dabrowiak et al. | |
| 2015/0230973 A1 | 8/2015 | Dabrowiak | |
| 2015/0230974 A1 | 8/2015 | Pistor | |
| 2015/0230975 A1 | 8/2015 | Dabrowiak et al. | |
| 2015/0314055 A1 | 11/2015 | Hogard | |
| 2016/0022477 A1 | 1/2016 | Schaefer | |
| 2016/0089184 A1 | 3/2016 | Truckai | |
| 2016/0131127 A1 | 5/2016 | Hendricks et al. | |
| 2016/0166758 A1 | 6/2016 | Norman et al. | |
| 2016/0228291 A1 | 8/2016 | Calliser | |
| 2016/0287432 A1 | 10/2016 | Dabrowiak et al. | |
| 2016/0287433 A1 | 10/2016 | Mazzone | |
| 2016/0287434 A1 | 10/2016 | Dabrowiak et al. | |
| 2016/0287435 A1 | 10/2016 | Pamichev et al. | |
| 2016/0290330 A1 | 10/2016 | Pamichev et al. | |
| 2018/0185192 A1 | 7/2018 | Mazzone | |
| 2018/0185193 A1 | 7/2018 | Mazzone | |
| 2018/0207024 A1 | 7/2018 | Dabrowiak | |
| 2018/0214302 A1 | 8/2018 | Dabrowiak | |
| 2018/0214303 A1 | 8/2018 | Dabrowiak | |
| 2018/0311072 A1 | 11/2018 | Pamichev | |
| 2018/0325725 A1 | 11/2018 | Dabrowiak | |
| 2019/0133820 A1 | 5/2019 | Jacobsen | |

FOREIGN PATENT DOCUMENTS

| | | |
|---|---|---|
| EP | 0663529 B1 | 5/1997 |
| GB | 1183185 A | 3/1970 |
| GB | 2040169 B | 3/1983 |
| GB | 2212262 A | 7/1989 |
| GB | 2383828 B | 6/2005 |
| JP | S61100243 A | 5/1986 |
| JP | 09215754 | 8/1997 |
| JP | 100127777 | 5/1998 |
| JP | 10305103 | 11/1998 |
| JP | 2001147095 A | 5/2001 |
| JP | 2002534160 | 10/2002 |
| JP | 2003028582 A | 1/2003 |
| JP | 2003508150 | 3/2003 |
| JP | 2003524507 A | 8/2003 |
| JP | 2008154751 | 7/2008 |
| JP | 2008531114 A | 8/2008 |
| JP | 2008539034 A | 11/2008 |
| JP | 2009500066 A | 1/2009 |
| JP | 2011505929 | 3/2011 |
| JP | 2011137621 A | 7/2011 |
| JP | 2011182849 | 9/2011 |
| JP | 2014023604 | 2/2014 |
| JP | 2017-505194 | 2/2017 |
| JP | 2017508509 | 3/2017 |
| JP | 2017511716 | 4/2017 |
| WO | 1990001682 A1 | 2/1990 |
| WO | WO 1993002730 | 2/1993 |
| WO | 1993004727 A1 | 3/1993 |
| WO | 1994000177 A1 | 1/1994 |
| WO | 1994001177 A1 | 1/1994 |
| WO | 9503680 A1 | 2/1995 |
| WO | 1997025011 A1 | 7/1997 |
| WO | 1998024491 A1 | 6/1998 |
| WO | 1998040017 A2 | 9/1998 |
| WO | 2000010494 A1 | 3/2000 |
| WO | 2001013809 A1 | 3/2001 |
| WO | 2001026719 A1 | 4/2001 |
| WO | 2001064146 A1 | 9/2001 |
| WO | 2001076517 A2 | 10/2001 |
| WO | 2001083001 A1 | 11/2001 |
| WO | 2005117546 A2 | 12/2005 |
| WO | 2006036585 A1 | 4/2006 |
| WO | WO 2009056640 | 5/2009 |
| WO | 2010040819 A1 | 4/2010 |
| WO | 2012175089 A1 | 12/2012 |
| WO | 2014160422 A1 | 10/2014 |
| WO | 2015119671 A1 | 8/2015 |
| WO | 2015122938 A1 | 8/2015 |
| WO | WO 2015119670 | 8/2015 |

OTHER PUBLICATIONS

Jeremy Thomas Dabrowiak, Eric Peterson, "Patient Heat Exchange System With Transparent Wall for Viewing Circulating Refrigerant", File History of related pending U.S. Appl. No. 14/276,202, filed May 13, 2014.

Jeremy Thomas Dabrowiak, Craig Wendell Pendry, Christoph Matthias Pistor, "Cold Plate Design in Heat Exchanger for Intravascular Temperature Management Catheter and/or Heat Exchange Pad", (56) References Cited

OTHER PUBLICATIONS

File History of related pending U.S. Appl. No. 14/675,504, filed Mar. 31, 2015.
American Urethane Inc., "Polyurethane Properties", available Oct. 12, 2010 http://web.archive.org/web/20101012211957/http://americanurethane.com/polyurethane-properties.html.
Dorraine Day Watts, Arthur Trask, Karen Soeken, Philip Perdue, Sheilah Dols, Christoph Kaufmann, "Hypothermic Coagulopathy in Trama: Effect of Varying Levels of Hypothermia on Enzyme Speed, Platelet Function, and Fibrinolytic Activity". The Journal of Trauma, Injury, Infection, and Critical Care, vol. 44, No. 5 (1998).
F.W. Behmann, E. Bontke, "Die Regelung der Wärmebildung bei künstlicher Hypothermie", Pflügers Archiv, Bd. 266, S. 408-421 (1958).
F.W. Behmann, E. Bontke, "Intravasale Kühlung", Pflügers Archiv, Bd. 263, S. 145-165 (1956).
Wilhelm Behringer, Stephanprueckner, Rainer Kenter, Samuel A. Tisherman, Ann Radovsky, Robert Clark, S. William Stezoski, Jeremy Henchir, Edwin Klein, Peter Safar, "Rapid Hypothermic Aortic Flush Can Achieve Survival without Brain Damage after 30 Minutes Cardiac Arrest in Dogs", 200 American Society of Anesthesiologist, Inc., Anesthesiology 2000; 93:1491-9.
Baharlou, "Written Opinion of the International Searching Authority", dated Oct. 12, 2017, from Counterpart PCT application PCT/US2016/024970.
Chinese Office Action in Application No. 201480077207.7, dated Jul. 3, 2019, 24 pages.
Dabrowiak "Heat Exchange System for Patient Temperature Control with Multiple Coolant Chambers for Multiple Heat Exchange Modalities", related pending U.S. Appl. No. 14/175,545 non-final office action dated Feb. 12, 2016.
Dabrowiak et al., "Fluid Cassette with Tensioned Polymeric Membranes for Patient Heat Exchange System", related pending U.S. Appl. No. 14/180,613, applicant's response to non-final office action filed Jun. 1, 2016.
Dabrowiak et al., "Heat Exchange System for Patient Temperature Control with Multiple Coolant Chambers for Multiple Heat Exchange Modalities" file history of related U.S. Appl. No. 14/175,545, filed Feb. 7, 2014.
Dabrowiak et al., "Patient Heat Exchange System with Transparent Wall for Viewing Circulating Refrigerant", related pending U.S. Appl. No. 14/276,202, applicant's response to non-final office action filed Jun. 1, 2016.
Dabrowiak et al., "Cold Plate Design in Heat Exchanger for Intravascular Temperature Management Catheter and/or Heat Exchange Pad", filed history of related U.S. Appl. No. 14/675,504, filed Mar. 31, 2015.
Dabrowiak et al., "Fluid Cassette with Tensioned Polymeric Membranes for Patient Heat Exchange System" file history of related U.S. Appl. No. 14/180,613, filed Feb. 14, 2014.
Dabrowiak et al., "Fluid Cassette with Tensioned Polymeric Membranes for Patient Heat Exchange System" file history of related pending U.S. Appl. No. 14/180,655 applicant's response to non-final office action filed Jun. 1, 2016.
Dabrowiak et al., "Fluid Cassette with Tensioned Polymeric Membranes for Patient Heat Exchange System" related pending U.S. Appl. No. 14/180,613, non-final office action dated May 19, 2016.
Dabrowiak et al., "Fluid Cassette with Tensioned Polymeric Membranes for Patient Heat Exchange System", related pending U.S. Appl. No. 14/180,613 final office action dated Jul. 15, 2016.
Dabrowiak et al., "Patient Heat Exchange System with Transparent Wall for Viewing Circulating Refrigerant" file history of related U.S. Appl. No. 14/275,202, filed May 13, 2014.
Dabrowiak et al., "Patient Heat Exchange System with Transparent Wall for Viewing Circulating Refrigerant", related pending application serial No. 14/276,202 final office action dated Jul. 15, 2016.
Dabrowiak et al., "Patient Heat Exchange System with Transparent Wall for Viewing Circulating Refrigerant", related pending U.S. Appl. No. 14/276,202, non-final office action dated May 19, 2016.
Dabrowiak et al., "Patient Heat Exchange System with Transparent Wall for Viewing Circulating Refrigerant", related pending U.S. Appl. No. 14/276,202, applicant's response to non-final office action dated Jun. 1, 2016.
Dabrowiak et al., "Patient Heat Exchange System with Transparent Wall for Viewing Circulation Refrigerant", related pending U.S. Appl. No. 14/276,202, applicant's response to non-final office action filed Aug. 21, 2018.
Dabrowiak et al., "Patient Heat Exchange System with Two and Only Two Fluid Loops", related U.S. Appl. No. 14/180,719, Non-Final Office Action dated Jun. 7, 2016.
Dabrowiak et al., "Patient Heat Exchange System with Two and Only Two Fluid Loops", related U.S. Appl. No. 14/180,719, Applicant's response to the Non-Final Office Action dated Sep. 7, 2016.
Dabrowiak et al., "Patient Heat Exchanger System with Transparent Wall for Viewing Circulation Refrigerant", related pending U.S. Appl. No. 14/276,202, non-final office action dated Feb. 21, 2018.
Dabrowiak et al., "Patient Heat Exchange System with Two and Only Two Fluid Loops", related U.S. Appl. No. 14/180,719, Applicant's Response to the Non-Final Office Action filed Sep. 7, 2016.
Dabrowiak, "Heat Exchange System for Patient Temperature Control With Multiple Coolant Chambers for Multiple Heat Exchange Modalities", File History of related pending U.S. Appl. No. 15/332,519, filed Oct. 24, 2016.
Dabrowiak, "Heat Exchange System for Patient Temperature Control with Multiple Coolant Chambers for Multiple Heat Exchange Modalities", file history of related U.S. Appl. No. 14/175,545, filed Feb. 7, 2014.
Dabrowiak, "Heat Exchange System for Patient Temperature Control with Multiple Coolant Chambers for Multiple Heat Exchange Modalities", related pending U.S. Appl. No. 14/175,545 applicants response to non-final office action dated May 2, 2016.
Dabrowiak, "Working fluid cassette with hinged plenum or enclosure for interfacing heat exchanger with intravascular temperature management catheter", filed history of related U.S. Appl. No. 14/676,672, filed Apr. 1, 2015.
European Office Action in Application No. 16775853.1, dated Nov. 6, 2019, 5 pages.
Extra Packaging Corp, Polyurethane Properties and Characteristics, accessed May 9, 2016 at http://www.extrapackaging.com/polyurethane/properites.php.
Hendricks et al., "Heat Exchange System for Patient Temperature Control with Easy Loading High Performance Peristaltic Pump" file history of related U.S. Appl. No. 14/534,718, filed Nov. 6, 2014.
Hendricks et al., "Heat Exchange System for Patient Temperature Control with Easy Loading High Performance Peristaltic Pump", related U.S. Appl. No. 14/534,718, Non-Final Office Action dated Jul. 25, 2016.
International Search Report dated Jun. 25, 2018 in related PCT Application No. PCT/US2018/016752, 4 pages.
International Search Report dated Jun. 25, 2018 in related PCT Application No. PCT/US2018/016754, 4 pages.
Japanese Office Action in Application No. 2018-118084, dated Sep. 2, 2019, 10 pages.
Japanese Office Action in Application No. 2018-160938, dated Jul. 19, 2019, 6 pages.
Mazzone, "Proximal Mounting of Temperature Sensor in Intravascular Temperature Management Catheter", file history of related U.S. Appl. No. 14/675,452, filed Mar. 31, 2015.
Pamichev et al., "Heat Exchange System for Patient Temperature Control With Easy Loading High Performance Peristatic Pump", file history of related U.S. Appl. No. 14/676,682, filed Apr. 1, 2015.
Pamichev et al., "Heat exchange system for patient temperature control with easy loading high performance penstatic pump", filed history of related U.S. Appl. No. 14/676,682, filed Apr. 1, 2015.
Pistor et al., "Fluid Cassette with Polymeric Membranes and Integral Inlet and Outlet Tubes for Patient Heat Exchange System" file history of related U.S. Appl. No. 14/180,655, filed Feb. 14, 2014.
Pistor et al., "Fluid Cassette with Polymeric Membranes and Integral Inlet and Outlet Tubes for Patient Heat Exchange System", related pending U.S. Appl. No. 14/180,655, applicant's response to non-final office action file Jun. 1, 2016.

(56) References Cited

OTHER PUBLICATIONS

Pistor et al., "Fluid Cassette With Polymeric Membranes and Integral Inlet and Outlet Tubes for Patient Heat Exchange System", related U.S. Appl. No. 14/180,655, Final Office dated Sep. 8, 2016.
Pistor et al., "Fluid Cassette with Polymeric Membranes and Integral Intel and Outlet Tubes for Patient Heat Exchange System", related pending U.S. Appl. No. 14/180,655, non-final office action dated May 18, 2016.
Wittman-Regis, "Written Opinion of the International Searching Authority", dated Oct. 12, 2017, from counterpart PCT application PCT/US2016/025030.
Japanese Office Action in Application No. 2019-018177, dated Mar. 31, 2020, 2 pages, English Translation.

\* cited by examiner

HEAT EXCHANGE SYSTEM FOR PATIENT TEMPERATURE CONTROL WITH MULTIPLE COOLANT CHAMBERS FOR MULTIPLE HEAT EXCHANGE MODALITIES

CROSS REFERENCE TO RELATED APPLICATIONS

This application is a continuation of U.S. application Ser. No. 14/175,545, filed on Feb. 7, 2014, the entire disclosure of which is incorporated herein by reference.

FIELD

The present application relates generally to heat exchange systems for patient temperature control with multiple coolant chambers for multiple heat exchange modalities.

BACKGROUND

Patient temperature control systems have been introduced to prevent fever in patients in the neuro ICU due to suffering from sub-arachnoid hemorrhage or other neurologic malady such as stroke. Also, such systems have been used to induce mild or moderate hypothermia to improve the outcomes of patients suffering from such maladies as stroke, cardiac arrest, myocardial infarction, traumatic brain injury, and high intracranial pressure. Examples of intravascular heat exchange catheters are disclosed in U.S. Pat. Nos. 6,419,643, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559, all of which are incorporated herein by reference.

External patient temperature control systems may be used. Such systems are disclosed in U.S. Pat. Nos. 6,827,728, 6,818,012, 6,802,855, 6,799,063, 6,764,391, 6,692,518, 6,669,715, 6,660,027, 6,648,905, 6,645,232, 6,620,187, 6,461,379, 6,375,674, 6,197,045, and 6,188,930 (collectively, "the external pad patents"), all of which are incorporated herein by reference.

In the present assignee's U.S. Pat. No. 7,070,612, also incorporated herein by reference, a heat exchange console that could receive the coils of working fluid loops of both an intravascular heat exchange catheter and an external heat exchange pad was described and patented. In general, in all of the intravascular and external patient temperature control solutions, the temperature of the working fluid flowing through the catheter or pad is regulated by a heat exchange console based on feedback provided by the patient's actual body temperature, typically core body temperature as may be variously measured rectally, esophageally, tympanic ear temperature, blood temperature in, e.g., the vena cava, etc. The working fluid temperature is regulated by thermally coupling the working fluid to heating and/or cooling elements in the console.

SUMMARY OF THE INVENTION

As understood herein, the working fluid of external pads, unlike that of intravascular catheters, may not be required to be sterile. Furthermore, as understood herein, the working fluid flow rate of external pads may be significantly greater than the flow rates of sterile working fluid through intravascular catheters. With these recognitions in mind, in some applications it may be desirable to use the same heat exchanger with both a catheter and a pad but two different working fluid pathways within the heat exchanger with respective different characteristics tailored to their respective heat exchange modalities (internal intravascular heat exchange with the blood using a catheter and external heat exchange through the skin using a pad).

As used herein, unless otherwise specifically delimited by claim language, "pad" means any device configured for placement against a patient's skin through which a working fluid, also referred to herein as a "coolant" regardless of whether removing or adding heat to the patient, can flow to exchange heat with a human patient.

A heat exchanger includes at least first and second heat exchange plate assemblies defining a first modality working fluid chamber between them. The first modality working fluid chamber is configured for receiving a holder through which sterile working fluid can flow to and from a first modality patient heat exchange member such that the sterile working fluid can exchange heat with the plate assemblies through the holder without the sterile working fluid touching the plate assemblies. At least a second modality working fluid chamber is defined in the heat exchanger through which second working fluid can flow to and from a second modality patient heat exchange member such that the second working fluid from the second modality patient heat exchange member can exchange heat with at least one of the plate assemblies by directly contacting the at least one the plate assemblies.

The first modality patient heat exchange member can be established by an intravascular heat exchange catheter, and the heat exchanger may include the first modality patient heat exchange member. On the other hand, the second modality patient heat exchange member can be established by an externally-applied exchange pad, and the system can include the pad. The second working fluid from the second modality patient heat exchange member need not be sterile.

In some examples, the second modality working fluid chamber includes a first sub-chamber in the first plate assembly and a second sub-chamber in the second plate assembly. Each plate assembly can include at least one respective refrigerant passageway through which refrigerant can flow to heat or cool the respective plate assembly. In example embodiments, refrigerant must flow in series through the refrigerant passageways such that all refrigerant must flow first through the refrigerant passageway of the first plate assembly before flowing through the refrigerant passageway of the second plate assembly. In other examples, refrigerant flows in parallel through the refrigerant chambers. In contrast, in example embodiments the second working fluid must flow in parallel through the first and second subchambers. Or, the second working fluid may flow in series through the first and second subchambers.

In another aspect, a system has at least first and second plate assemblies through which refrigerant can flow through respective first and second refrigerant chambers. The plate assemblies define a slot between them that can receive first working fluid from an intravascular heat exchange catheter, so that the first working fluid from the catheter can be heated or cooled by the refrigerant flowing through the refrigerant chambers. The plate assemblies further include respective first and second working fluid chambers laterally outboard the respective first and second refrigerant chambers and configured for receiving second working fluid from an external heat exchange pad to facilitate heat exchange between the second working fluid and the refrigerant.

In another aspect, a system includes a first plate and a first working fluid chamber on a first side of the first plate. A first refrigerant chamber is on a second side of the first plate opposite the first side, such that heat exchange is facilitated through the first plate between the first refrigerant chamber and the first working fluid chamber. A second working fluid chamber is separated from the first refrigerant chamber by a wall through which heat exchange may be effected between the second working fluid chamber and the first refrigerant chamber.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
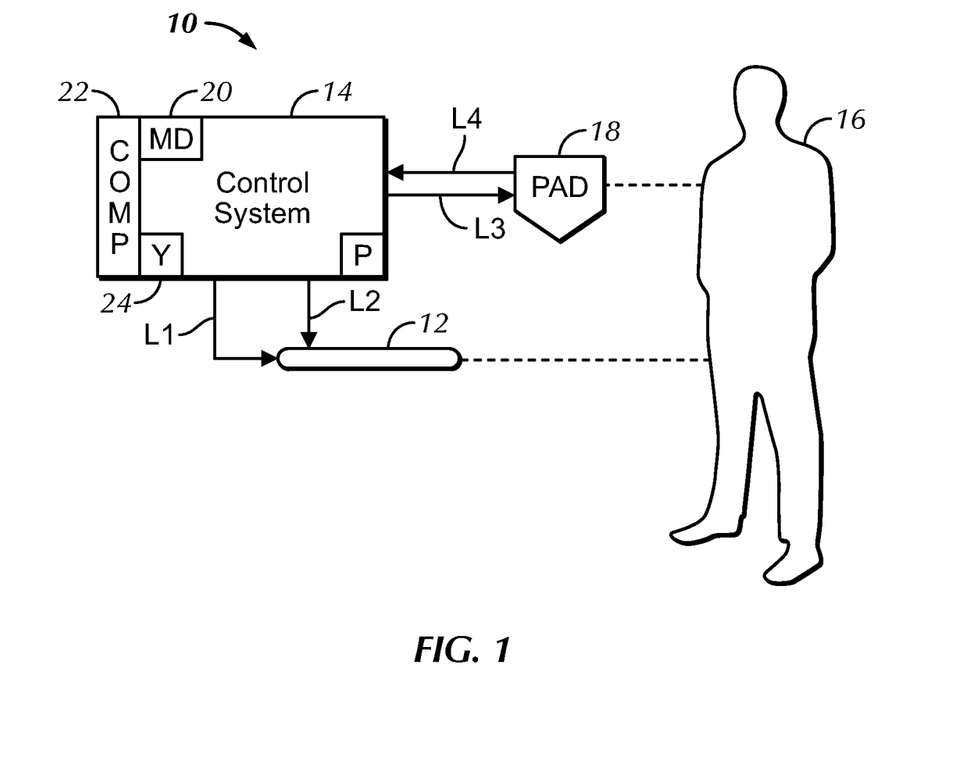
FIG. 1 is a schematic view of a non-limiting system in accordance with the present invention.

Referring initially to FIG. 1, in accordance with present principles, a system 10 may include an intravascular heat exchange catheter 12 controlled by a control system 14 to control patient temperature, e.g., to prevent the patient 16 from becoming febrile or to induce therapeutic hypothermia in the patient 16. In the catheter, working fluid (also referred to as "coolant") such as but not limited to saline circulates (typically under the influence of a pump "P" in the control system) in a closed loop from the control system 14, through a fluid supply line L1, through the catheter 12, and back to the system 14 through a fluid return line L2, such that no coolant enters the body. While certain preferred catheters are disclosed below, it is to be understood that other catheters can be used in accordance with present principles, including, without limitation, any of the catheters disclosed above or in the following U.S. patents, all incorporated herein by reference: U.S. Pat. Nos. 5,486,208, 5,837,003, 6,110,168, 6,149,673, 6,149,676, 6,231,594, 6,264,679, 6,306,161, 6,235,048, 6,238,428, 6,245,095, 6,251,129, 6,251,130, 6,254,626, 6,261,312, 6,312,452, 6,325,818, 6,409,747, 6,368,304, 6,338,727, 6,299,599, 6,287,326, 6,126,684. The catheter 12 may be placed in the venous system, e.g., in the superior or inferior vena cava.

Instead of or in addition to the catheter 12, the system 10 may include one or more pads 18 that are positioned against the external skin of the patient 16 (only one pad 18 shown for clarity). The pad 18 may be, without limitation, any one of the pads disclosed in the external pad patents. The temperature of the pad 18 can be controlled by the control system 14 to exchange heat with the patient 16, including to induce therapeutic mild or moderate hypothermia in the patient in response to the patient presenting with, e.g., cardiac arrest, myocardial infarction, stroke, high intracranial pressure, traumatic brain injury, or other malady the effects of which can be ameliorated by hypothermia. The pad 18 may receive working fluid from the system 14 through a fluid supply line L3, and return working fluid to the system 14 through a fluid return line L4.

The control system 14 may include one or more microprocessors 20 receiving target and patient temperatures as input and controlling, among other things, the pump "P" and a refrigerant compressor 22 with a bypass valve 24 that can be opened to permit refrigerant to bypass the compressor. The refrigerant circulates through a heat exchanger within the control system 14 and described further below.

Figure 2:
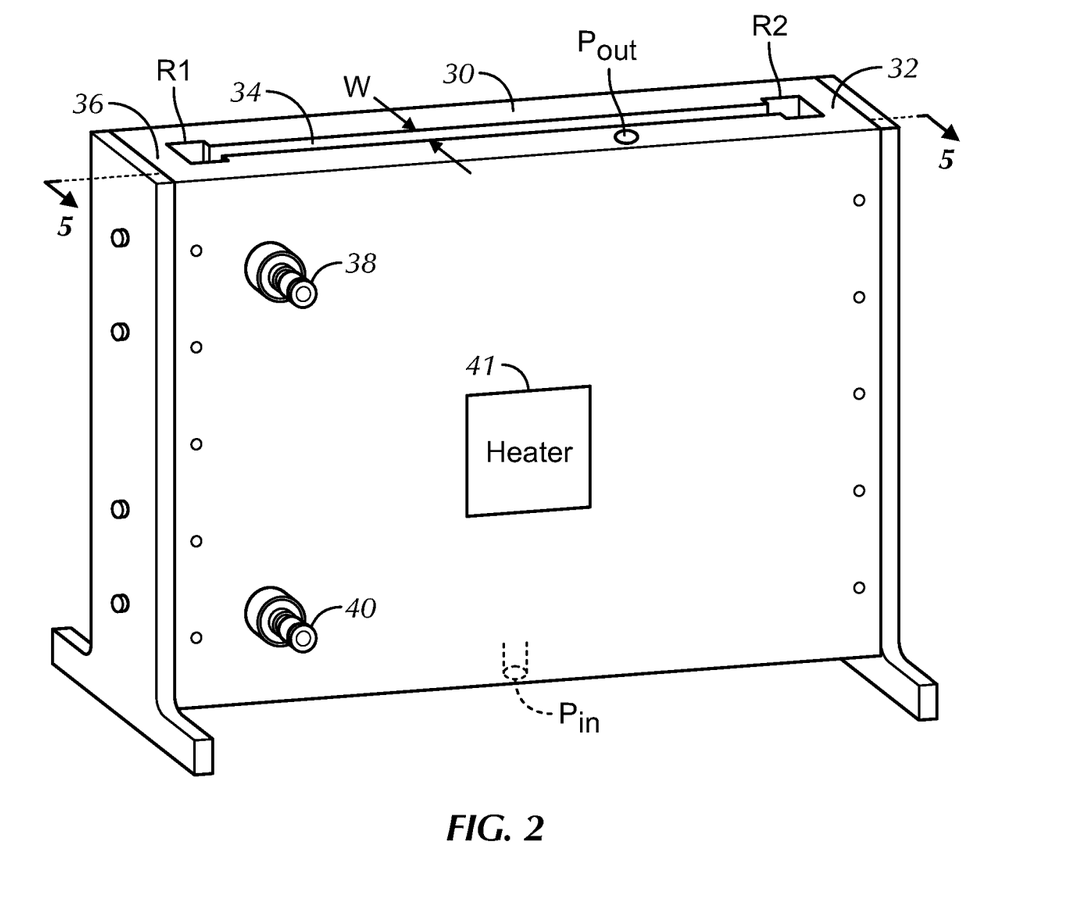
FIG. 2 is a perspective view of an example working fluid cassette holder portion of a heat exchange system.

Indeed and now referring to FIG. 2, a portion of an example heat exchanger in the control system 14 is shown which includes at least two cold plates 30, 32 defining a cassette slot 34 between them. In one embodiment, the width "W" of the slot 34 is less than forty mils (0.040"), and may be between twenty nine mils and thirty one mils (0.029"-0.031"). In a specific example the width "W" may be thirty mils. As further detailed below, the slot 34 may establish a coolant chamber to receive a heat exchange member such as but not limited to a cassette through which working fluid from an intravascular heat exchange catheter flows. Because heat exchange is effected through the walls of the heat exchange member, the working fluid from the catheter does not contact any surface or fluid in the heat exchanger of the control system 14 outside the walls of the heat exchange member. In this way, the working fluid, typically saline in non-limiting examples, circulating through the intravascular catheter can remain sterile. Accordingly, attention will first focus on the coolant chamber established by the slot 34.

The cold plates 30, 32 may be made of metal, and can be rectilinear as shown and indeed may be nearly square. The cold plates 30, 32 may abut each other along left and right side walls 36, with elongated vertical cassette frame receptacles R1 and R2 being located immediately inboard of the respective side walls 36 and with the slot 34 extending between the walls 36 and terminating at the receptacles R1, R2 as shown. The frame receptacles R1, R2 may be wider than the slot 36.

In the example shown, refrigerant inlet and outlet tubes 38, 40 extend through at least one of the cold plates 32 to communicate refrigerant from a compressor into a refrigerant passageway in the cold plate, which establishes a second coolant chamber in addition to (and in thermal contact with) the first coolant chamber established by the slot 34. Each cold plate may have its own refrigerant inlet and outlet tubes, or, in the embodiment shown, only one cold plate may be formed with refrigerant inlet and outlet tubes and the other cold plate either thermally coupled to the cold plate in which the refrigerant flows and/or receiving refrigerant from the other cold plate through passageways formed through one or both of the side walls 36.

In one example, pad working fluid inlet and outlets $P_{in}$ and $P_{out}$ may also be formed in at least one of the cold plates as shown. As discussed in greater detail below, working fluid from the pad 18 via lines L3 and L4 may be ported into the pad working fluid inlet and outlets $P_{in}$ and $P_{out}$ to exchange heat with the refrigerant flowing through the cold plates. Also, to provide for warming working fluid, one or more electric heaters 41 may be mounted on one or both of the cold plates to heat the cold plates. Alternatively to warm the cold plates, the bypass valve 24 (FIG. 1) may be opened to allow hot gaseous refrigerant from the compressor to bypass the condenser as the gaseous refrigerant circulates through the system.

Figure 3:
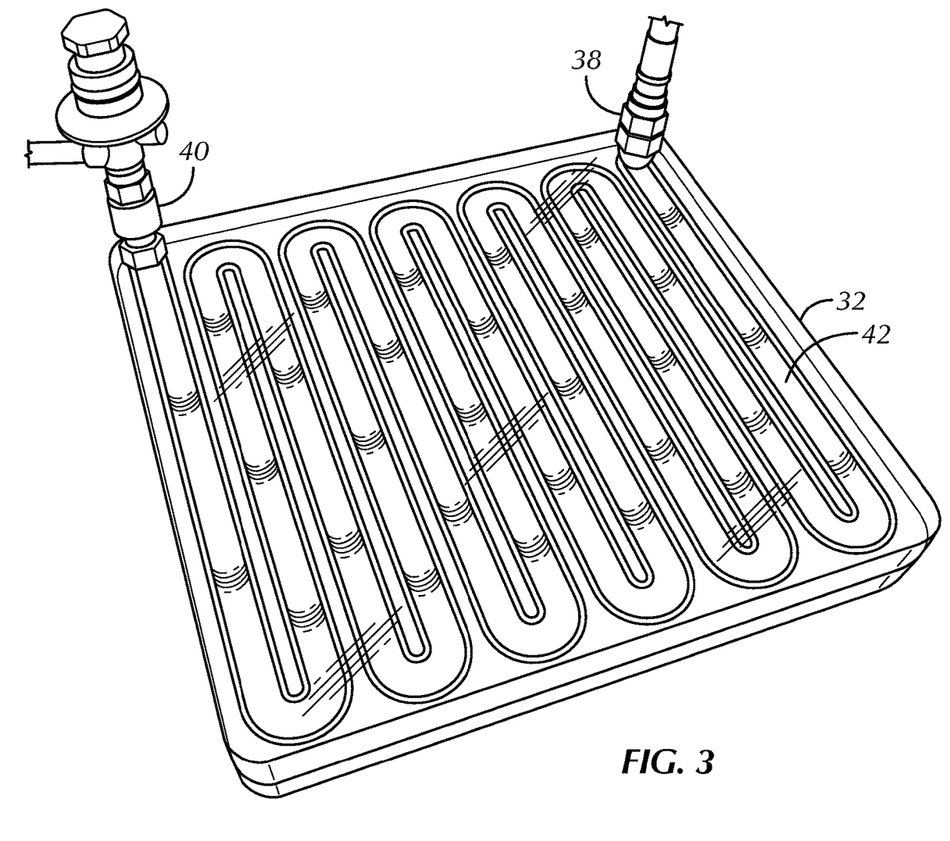
FIG. 3 is a perspective view of one half of the cassette holder shown in FIG. 2, with the opaque metal inner surface shown in transparency to reveal the serpentine refrigerant passageway.

FIG. 3 shows details of an example cold plate 32 looking at the inner surface in transparency, it being understood that the inner surface typically is metal and that the serpentine refrigerant passageway 42 shown in FIG. 3 typically would not be visible to the human eye. In any case, the example refrigerant passageway that fluidly connects the refrigerant inlet 38 to the refrigerant outlet 40 may be serpentine-shaped as shown, or may be some other shape or pattern such as a herringbone pattern a wave pattern, etc.

Figure 4:
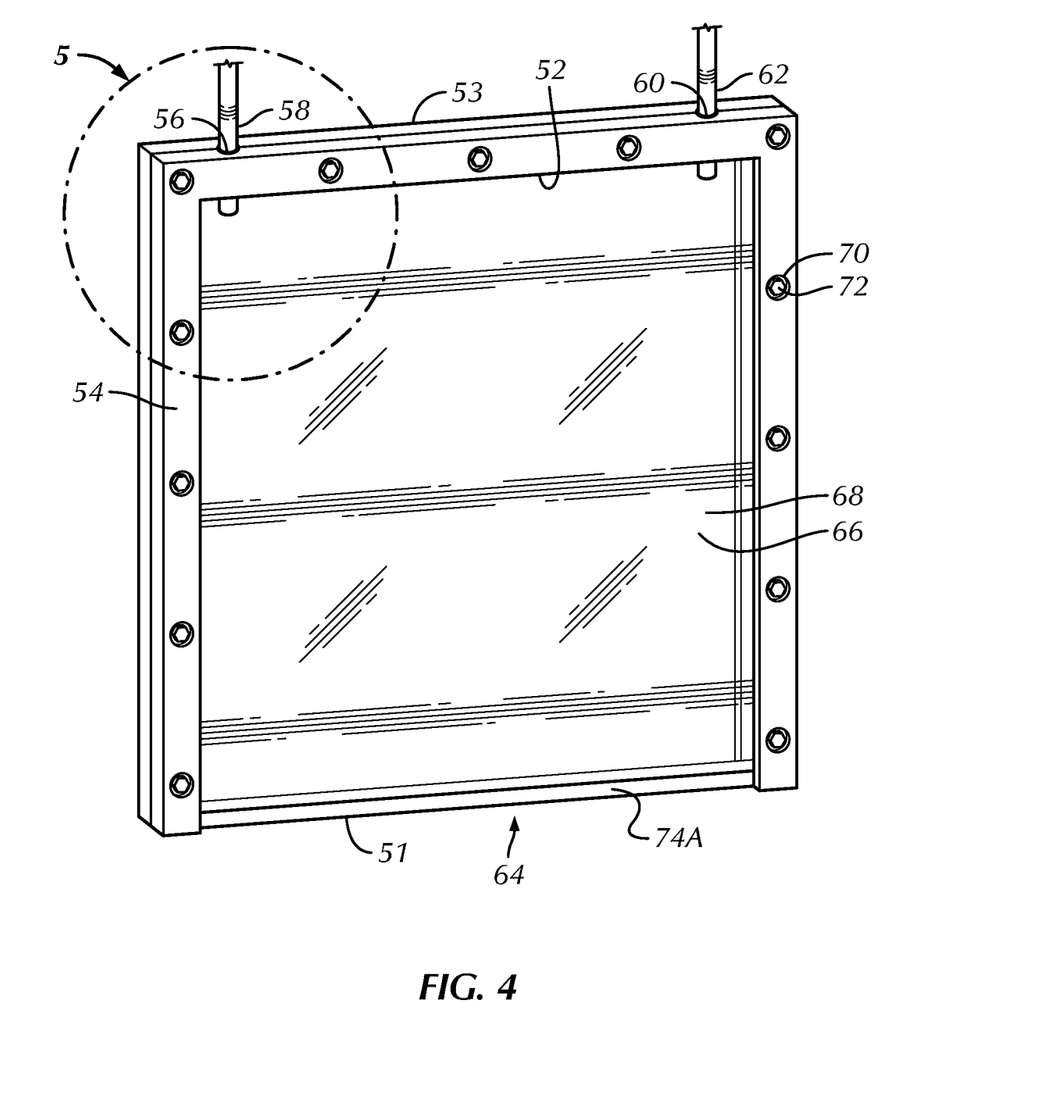
FIG. 4 is a perspective view of an example working fluid cassette configured to engage the cassette holder shown in FIGS. 2 and 3.

FIG. 4 shows an example working fluid cassette 50 according to present principles. The cassette 50 is configured to fit snugly into the slot 34 and cassette frame receptacles R1, R2 defined between the cold plates 30, 32. Working fluid such as saline from a patient-engageable heat exchange member such as the catheter 12 flows through the cassette 50 in operation, with the working fluid exchanging heat with the refrigerant in the cold plates. In example embodiments, the cassette 50 is a low cost single-use disposable item that can contain, e.g., sterile saline which circulates through the catheter 12. The cassette may be placed by a medical caregiver in the slot 34 between the cold plates 30, 32 and the membrane portion which defines a space or working fluid chamber through which the example saline flows inflates when the working fluid flows through it, achieving thermal contact with the cold plates 30, 32.

In the example shown, the cassette 50 includes a frame 52 defining a periphery and a preferably rectilinear opening bounded as shown on at least three sides by the periphery of the frame. In the non-limiting example shown, the frame includes an elongated parallelepiped-shaped top rail 53 and elongated parallelepiped-shaped left and right side rails 54 parallel to each other and perpendicular to the top rail 32. The example frame 52 may have a metal strip or bottom rail 51 opposite the top rail and connected to the left and right side rails to support the membrane and facilitate placing the membrane in biaxial tension. In any case, the example frame 52 is rectilinear and is configured for being closely received between the two cold plates 30, 32, with the side rails 54 slidably engageable with the frame receptacles R1, R2 between the cold plates 30, 32 and with the below-described membrane assembly passed through the slot 36 to be in close juxtaposition with the refrigerant channels in the cold plates.

In FIG. 4, the frame, in the example shown, the top rail 53 thereof, is formed with a fluid inlet 56 in which an inlet tube 58 has been disposed and a fluid outlet 60 in which an outlet tube 62 has been disposed. Both the inlet and outlet establish respective fluid passageways through the frame into the opening. The inlet and outlet tubes 58, 62 may be engaged with the fluid return and supply lines L1, L2 that are associated with the catheter 12. The tubes 58, 62 may terminate at just below the top rail 53 (FIG. 4), or they may extend any desired length down to the bottom of the assembly, i.e., the tubes 58, 62 may extend almost the entire length of the left and right side rails 54, ending just above the below-described bottom seam of the membrane assembly.

Indeed, a polymeric membrane assembly 64 is connected to the frame 52, blocking the opening that is bounded on four sides by the frame as shown. The membrane assembly includes a first membrane 66 that is parallel to and closely spaced from a second membrane 68, leaving a space therebetween which establishes a working fluid chamber. The fluid inlet 56 and fluid outlet 60 communicate with the space between the membranes 66, 68. At least one and preferably both of the membranes 66, 68 are disposed in tension in the opening. The space between the membranes is expandable when filled with working fluid.

In one example, each membrane is no more than two mils (0.002") thick and more preferably is between one mil and two mils in thickness (0.001"-0.002"), inclusive. The example preferred membranes 66, 68 are co-extensive with the opening and like the opening are more or less square, with the length of top and bottom edges of the example membranes being approximately equal (within±10% and more preferably within±5%) of the lengths of the left and right edges of the membranes. In other embodiments instead of a square (1:1) aspect ratio, an aspect ratio of up to 1:1.5 may be used. The working fluid chamber between the membranes is also rectilinear and in the preferred embodiment no obstructions exist between the membranes, meaning the working fluid chamber is a complete rectilinear, more or less square chamber.

Owing to the thinness of the membranes 66, 68 and the closeness of the cold plates 30, 32 to each other and to the membrane assembly between them when the cassette is engaged with the cold plates, the system shown in the figures affords low impedance of heat transfer between the refrigerant circulating in the cold plates and the working fluid circulating between the membranes 66, 68. The working fluid chamber between the membranes inflates due to backpressure generated by working fluid flow, eliminating or reducing the need for a moving mechanism in the cold plates. Moreover, the narrow slot 34 between the two cold plates provides better heat transfer by reducing the conductive path length between the cold plates and the working fluid. The frame allows for ease of handling, such as insertion and removal of the cassette with/from the cold plates.

With respect to the example working fluid chamber between the membranes 66, 68 having a width-to-length aspect ratio near 1:1 (i.e., square or nearly so), the amount of backpressure required to induce working fluid flow through heat exchanger is reduced compared to a less square configuration. This reduces the amount of work that a working fluid pump must perform, which is desirable for two reasons. One, since the pump may be disposable, lower performance requirements translate into a lower cost disposable and quieter system. For instance, peristaltic roller pumps offer quiet operation and a low-cost disposable element, but operate most efficiently when only modest pressures are required. Two, lowering the working fluid pump work reduces the amount of heat transferred into the working fluid by the pump itself. Also, a low width/length aspect ratio results in slower working fluid velocity which reduces amount of mixing, but this otherwise desirable (from a heat exchange standpoint) effect is negligible in the present example system since the Reynolds numbers are typically<1000, suggesting a laminar flow regime. Furthermore, a low width/length aspect ratio significantly reduces the number of bends (or "corners") in the fluid flow path. These bends are areas of mixing for the fluid which promotes heat transfer. Without them, a fluid boundary layer builds up. However, this effect is offset herein by maintaining a narrow slot between the cold plates. This way the primary heat transfer mechanism is by conduction, but the conduction path length (and therefore boundary layer) is small, resulting in a relatively high rate of heat transfer.

In preferred examples, the membranes 66, 68 are stretched under tension during assembly to the frame, preferably biaxially (i.e., in tension between the top and bottom rails 53, 51 and also in tension between the left and right side rails 54). This tension can be maintained over the shelf life of the product. Pretensioning minimizes wrinkles in material, which is beneficial because wrinkles can impede working fluid flow and create air gaps which reduce heat transfer between the working fluid and cold plates. Wrinkles can also complicate insertion of the membrane assembly into the narrow slot 34.

To establish pre-tensioning of the membranes, the frame may be made in halves and posts such as threaded fasteners can extend transversely to one half of the frame, with the membranes 66, 68 being stretched over the posts and holes made in the membranes to receive the posts. The other half of the frame is then positioned to sandwich a rectilinear border portion of the membrane assembly between the frame halves, and a closure such as respective nuts engaged with the posts to hold the frame halves together with the membrane assembly held in tension between the frame halves. FIG. 4 shows that the working fluid chamber is closed off at the bottom by a bottom seam 74A of the membrane assembly, which is part of the border portion 74. In addition to applying tension to avoid wrinkling during use, additional posts may be used to avoid wrinkling during the welding process, improving the quality of the weld joints.

In the border portion 74, at least one and preferably more layers of polymer film may be used to reinforce the membranes 66, 68 to establish welded seams through which (at the sides of the membrane assembly) the post holes are formed, allowing for easier fabrication. By placing reinforcing layers on the border portion 74 only, the central "window" of the membrane assembly consists only of a single thin layer membrane between the working fluid and one of the cold plates 30, 32 to minimize impeding heat transfer. A die-cut reinforcement layer may be used which reinforces the entire perimeter with one piece of material.

In some examples, the polymer membranes 66, 68 are highly stretchable, at least greater than 25% elongation. This allows the membranes to change from the empty flat state shown in FIG. 4 to an inflated shape (within the slot 34 between the cold plates) without wrinkling. It also allows the membranes to easily conform to features on the faces of the cold plates.

Additionally, the membranes may be made of a material which can also be made into tubing. Tubes such as the inlet and outlet tubes 58, 62 shown in FIG. 4 can then be thermally welded (e.g., using RF sealing) to the membranes, which is more reliable and quicker than adhesive bonding. The membranes 66, 68 need not provide their own lateral support because the cold plates 32, 34 and frame provide the support for the inflated membrane assembly, allowing it to withstand the pressure generated as a result of working fluid flowing through between the membranes. Structural features such as raised bumps, concavities, raised ribs, and so on may be located on the cold plates to optimize heat transfer. This can be economically advantageous because the cold plates are reusable components. Manifolds can be cut into the cold plates to even out the distribution of saline flow.

Figure 5:
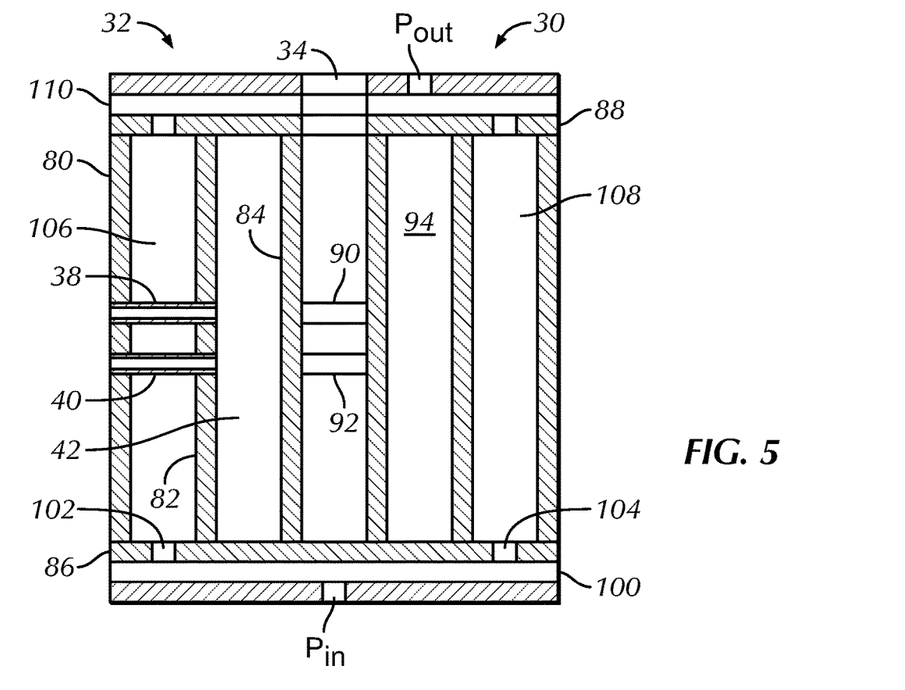
FIG. 5 is a cross-sectional view as seen along the line 5-5 in FIG. 2.

Having described an example non-limiting thermal exchange combination of structure between the heat exchanger in the control system 14 and the sterile working fluid in the intravascular temperature control catheter 12, attention is now directed to FIG. 5, which shows an example embodiment of additional coolant chambers in the cold plates by which to effect heat exchange with working fluid, including non-sterile working fluid, from the external heat exchange pad 18. Note that the plate structures shown in FIG. 5 preferably are metal or other material with high heat conductivity.

As shown, the cold plates 30, 32 may be multi-plate assemblies defining multiple fluid chambers, although in the discussion below they are referred to generally as "plates" 30 and 32. In the non-limiting example shown, the refrigerant inlet and outlet tubes 38, 40 extend through an outer wall 80 and a separator wall 82 of the cold plate 32 to communicate refrigerant from the compressor 22 into the refrigerant passageway 42 in the cold plate, which establishes a refrigerant chamber 83 that is bounded by the separator wall 82 and an inner wall 84. On the other side of the inner wall 84 is the catheter working fluid cassette slot 34. As stated earlier, each cold plate may have its own refrigerant inlet and outlet tubes, or only one cold plate may be formed with refrigerant inlet and outlet tubes and the other cold plate either thermally coupled to the cold plate in which the refrigerant flows and/or receiving refrigerant from the other cold plate through passageways formed between the cold plates. In the example shown, the cold plates 30, 32 are thermally coupled through the side walls 36 (FIG. 2), a common bottom wall 86 (FIG. 5), and through the uninterrupted portions of a top wall 88 in which the slot 34 is formed.

In some examples, the cold plates 30, 32 are mirror image structures of each other. In the example of FIG. 5, the refrigerant chamber in the left-hand cold plate (32) is in fluid communication through refrigerant supply and return passageways 90, 92 with a refrigerant chamber 94 in the right-hand cold plate 30. Thus, the refrigerant chambers of the cold plates straddle the cassette slot 34 and are separated therefrom by respective inner walls 84, with refrigerant flowing serially through the left and right refrigerant chambers, first from the refrigerant inlet tube 38 into the left refrigerant chamber, then through the refrigerant supply passageway 90, the left hand refrigerant chamber 94, back through the refrigerant return passageway 92, and out the refrigerant outlet tube 40. This increases the refrigerant fluid flow rate through the refrigerant chambers, when two refrigerant chambers are provided as in the example shown.

In contrast, pad working fluid channel fluid flow may be plumbed in parallel to left and right pad fluid chambers 96, 98, which straddle the refrigerant chambers as shown and are separated therefrom by respective separator walls 82. In the non-limiting example shown, fluid from the external pad flows through the pad working fluid inlet $P_{in}$ into an inlet plenum 100 formed in the bottom wall 86. The fluid flows in parallel through inlet ports 102, 104 into left and right pad working fluid chambers 106, 108. The fluid exits the pad working fluid chambers through an upper plenum 110 formed in the top plate 88 and out of the working fluid outlet $P_{out}$ back to the external pad. This example parallel fluid flow reduces backpressure in the pad working fluid system.

Note that the above-described series fluid flow through the refrigerant chambers and parallel flow through the pad working fluid chambers is exemplary only, and is not limiting. Thus, fluid flow through the pad working fluid chambers may be in series and/or fluid flow through the refrigerant chambers may be parallel. Note further that the particular example plumbing arrangements illustrated and described are but one example of plumbing fluid through the multi-chamber cold plates 30, 32.

Figure 6:
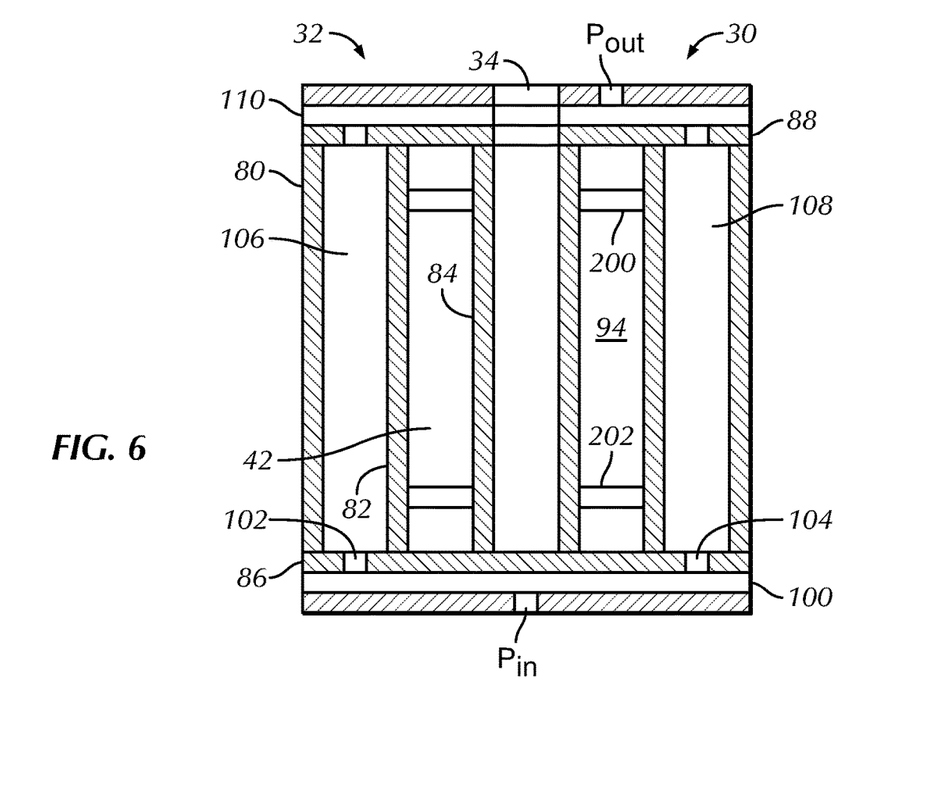
FIG. 6 is a cross-sectional view of an alternate embodiment as would be seen along the line 5-5 in FIG. 2.

Indeed, FIG. 6 shows a system similar to the one shown in FIG. 5, except that fluid flow through the refrigerant chambers is in parallel. Both refrigerant chambers may communicate with a refrigerant inlet plenum 200 through which refrigerant flows into each refrigerant chamber 94 in parallel. Also, both refrigerant chambers may communicate with a refrigerant outlet plenum 202 through which refrigerant flows out of each refrigerant chamber 94 in parallel back to the compressor.

It may now be appreciated that in the intravascular heat exchange mode, working fluid from the catheter 12 flowing through the cassette 50 which is disposed in the slot 34 exchanges heat with the refrigerant in the refrigerant chambers 42, 94 through the respective inner walls 84. The catheter working fluid comes into contact with no portion of the cold plate heat exchanger, owing to it flowing through the cassette 50. In this way, the catheter working fluid retains its sterility and is enclosed in a closed fluid circuit for withstanding circulation fluid pressures of, e.g., seventy pounds per square inch (70 psi).

On the other hand, since pad working fluid is separated from the patient by an external pad, it may not require sterility, in which case the pad working fluid contacts the separator plates 82 directly in the cold plates 30, 32 to exchange heat with the refrigerant in the refrigerant chambers 42, 94.

While the particular HEAT EXCHANGE SYSTEM FOR PATIENT TEMPERATURE CONTROL WITH MULTIPLE COOLANT CHAMBERS FOR MULTIPLE HEAT EXCHANGE MODALITIES is herein shown and described in detail, the scope of the present invention is to be limited by nothing other than the appended claims.

What is claimed is:

1. Apparatus, comprising:
   at least first and second heat exchange assemblies each including a first working fluid chamber, the first and second heat exchanged assemblies being configured for receiving a holder through which a first working fluid is configured to flow to and from a patient heat exchanger such that the first working fluid can exchange heat with the heat exchange assemblies through the holder without the first working fluid touching the heat exchange assemblies; and
   for each of the first and second heat exchange assemblies, at least a second working fluid chamber that is laterally outboard the first working fluid chamber, wherein at least the first heat exchange assembly includes at least one passageway through the first working fluid chamber, the second working fluid chamber, or each of the first and second working fluid chambers, the passageway through which a second working fluid can flow to exchange heat with at least the first working fluid.

2. The apparatus of claim 1, wherein the patient heat exchanger is established by an intravascular heat exchange catheter.

3. The apparatus of claim 1, wherein the patient heat exchanger is connected to the holder that is received by the first and second heat exchange assemblies.

4. The apparatus of claim 1, wherein the patient heat exchanger is established by an externally-applied exchange pad.

5. The apparatus of claim 1, comprising a second patient heat exchanger having a different heating modality than the patient heat exchanger.

6. The apparatus of claim 5, wherein the second working fluid from the second patient heat exchanger is not sterile.

7. The apparatus of claim 1, wherein the second working fluid chamber includes a first sub-chamber in the first heat exchange assembly and a second sub-chamber in the second heat exchange assembly.

8. The apparatus of claim 1, wherein the second working fluid must flow in series through the first and second heat exchange assemblies such that all of the second working fluid must flow first through the first heat exchange assembly before flowing through the second heat exchange assembly.

9. The apparatus of claim 1, wherein the second working fluid can flow in parallel through the first and second heat exchange assemblies.

10. The apparatus of claim 7, wherein the second working fluid must flow in parallel through the first and second subchambers.

11. A method comprising:
    flowing refrigerant through at least first and second assemblies having respective first and second refrigerant chambers;
    receiving, in a region between the first and second assemblies, first working fluid from a catheter so that the first working fluid from the catheter can be heated or cooled by the refrigerant flowing through the refrigerant chambers; and
    receiving, in respective first and second working fluid chambers laterally outboard the respective first and second refrigerant chambers, second working fluid from a heat exchanger configured for exchanging heat with an external surface of a patient to facilitate heat exchange between the second working fluid and the refrigerant.

12. The method of claim 11, wherein the region is configured for receiving a cassette through which the first working fluid can flow so that heat can be exchanged between the first and second assemblies and the first working fluid without the first working fluid contacting the first and second assemblies.

13. The method of claim 11, comprising establishing fluid communication between the catheter and the first and second assemblies.

14. The method of claim 11, comprising exchanging, in response to receiving the second working fluid from the heat exchanger, heat with the external surface of the patient.

15. The method of claim 11, comprising flowing refrigerant in series through the refrigerant chambers such that all refrigerant flows first through the refrigerant chamber of the first assembly before flowing through the refrigerant chamber of the second assembly.

16. The method of claim 11, comprising flowing refrigerant in parallel through the refrigerant chambers.

17. The method of claim 11, comprising flowing the second working fluid in parallel through the first and second working fluid chambers.

18. System comprising:
    first heat transmitting member;
    first working fluid chamber on a first side of the first heat transmitting member;
    first refrigerant chamber on a second side of the first heat transmitting member opposite the first side, such that heat exchange is facilitated through the first heat transmitting member between the first refrigerant chamber and the first working fluid chamber; and
    second working fluid chamber separated from the first refrigerant chamber by a barrier through which heat exchange may be effected between the second working fluid chamber and the first refrigerant chamber.

19. The system of claim 18, comprising:
    second heat transmitting member, the first working fluid chamber being between the first and second heat transmitting members;
    second refrigerant chamber on a side of the second heat transmitting member opposite the first working fluid chamber, such that heat exchange is facilitated through the second heat transmitting member between the second refrigerant chamber and the first working fluid chamber; and third working fluid chamber separated from the second refrigerant chamber by a barrier through which heat exchange may be effected between the third working fluid chamber and the second refrigerant chamber.

\* \* \* \* \*

UNITED STATES PATENT AND TRADEMARK OFFICE
CERTIFICATE OF CORRECTION

PATENT NO. : 10,828,189 B2
APPLICATION NO. : 15/332519
DATED : November 10, 2020
INVENTOR(S) : Jeremy Thomas Dabrowiak Page 1 of 1

It is certified that error appears in the above-identified patent and that said Letters Patent is hereby corrected as shown below:

In the Specification

Column 1, Line 9, after "2014,", insert -- now U.S Patent No. 9,474,644, --

In the Claims

Column 9, Line 31, Claim 1, delete "exchanged" and insert -- exchange --

Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*